(12) United States Patent　　(10) Patent No.: US 6,808,505 B2
Kadan　　(45) Date of Patent: *Oct. 26, 2004

(54) DIAGNOSTIC NEEDLE ARTHROSCOPY AND LAVAGE SYSTEM

(76) Inventor: Jeffrey S. Kadan, 216 Via Linda Vista, Redondo Beach, CA (US) 90277

( * ) Notice: Subject to any disclaimer, the term of this patent is extended or adjusted under 35 U.S.C. 154(b) by 85 days.

This patent is subject to a terminal disclaimer.

(21) Appl. No.: 10/371,060

(22) Filed: Feb. 21, 2003

(65) Prior Publication Data

US 2004/0082915 A1 Apr. 29, 2004

Related U.S. Application Data

(63) Continuation-in-part of application No. 10/165,691, filed on Jun. 7, 2002, now abandoned, and a continuation of application No. 09/570,324, filed on May 12, 2000, now Pat. No. 6,428,510, and a continuation of application No. 09/495,601, filed on Feb. 1, 2000, now Pat. No. 6,419,654.

(51) Int. Cl.⁷ ............................................. A61M 1/00
(52) U.S. Cl. .................................... 604/27; 604/164.04
(58) Field of Search ............................. 604/27, 164.07, 604/30, 33, 35, 43, 44, 45, 306, 511; 606/53, 167, 185; 600/101, 104

(56) References Cited

U.S. PATENT DOCUMENTS 6,419,654 B1 * 7/2002 Kadan .......................... 604/27

* cited by examiner

Primary Examiner—Edward K. Look
Assistant Examiner—Vinod D. Patel
(74) Attorney, Agent, or Firm—David O'Reilly (57) ABSTRACT

A system for performing diagnostic needle arthroscopy and lavage through a single port of entry into the joint compartment. The system is comprised of a handpiece having valves for irrigation and suctioning, a diagnostic cannula attached to the handpiece. The system includes a mobile cart, camera, a high-resolution monitor and an air compressor to power individually controlled irrigation pumps to deliver irrigation fluid to a handpiece and a vacuum suction console to collect fluid. The system also includes a biopsy cannula that can be exchanged for the diagnostic cannula using an exchange rod. The biopsy cannula is comprised of a pair of piggyback cannulas, one for visualization, diagnosis, irrigation and suction while the other is for insertion of a biopsy instrument or surgical devices. The biopsy instrument is comprised of a thin shaft connected to forceps at a distal end for performing surgical procedures.

25 Claims, 9 Drawing Sheets

DIAGNOSTIC NEEDLE ARTHROSCOPY AND LAVAGE SYSTEM

This application is a Continuation-In-Part of application Ser. No. 10/165,691 filed Jun. 7, 2002 now abandoned and a Continuation of application Ser. No. 09/570,324, filed May 12, 2000 now U.S. Pat. No. 6,428,510, and application Ser. No. 09/495,601 filed Feb. 1, 2000 now U.S. Pat. No. 6,419,654.

BACKGROUND OF THE INVENTION

1. Field of the Invention

This invention relates to systems to perform arthroscopies of joints such as the knee and more particularly relates to a diagnostic needle arthroscopy and lavage, (DNAL) system for performing arthroscopies through a single port.

2. Background Information

Arthroscopy is a surgical procedure in which an endoscope (arthroscope) is inserted into a joint. Fluid is then injected into the joint to slightly distend the joint and allow visualization of structures within the joint. Surgery is usually viewed on a monitor so that the whole operating team can visualize the surgical procedure that is being performed. The arthroscopy procedure falls into two types; operative and diagnostic. Operative arthroscopy is more interventional, utilizing larger devices and multiple ports to accomplish a variety of procedures designed to repair internal derangement or tears of intra-articular structures. Diagnostic arthroscopy is less invasive, requiring smaller devices and a single port of entry into the joint. Operative arthroscopes are typically four (4) mm in diameter. The operative arthroscopic procedure is often conducted under general anesthesia and is used to examine and treat the inside of the joint for damaged tissue. Most common types of surgery using operative arthroscopic procedures includes the removal or repair of torn meniscus (cartilage), ligament reconstruction, removal of loose debris and trimming or shaving damaged cartilage. Diagnostic arthroscopy is done under local anesthetic only and is most often accompanied by a thorough rinsing out of the joint (lavage).

The value of arthroscopy as a diagnostic and-therapeutic tool is well recognized by physicians. Recent advances have made it technically feasible to perform diagnostic needle arthroscopy procedures in a physician's office using a small, 1.7 mm fiberoptic arthroscope. Generally the diagnostic needle arthroscopy and lavage procedure is used to diagnose and evaluate joint pathology and relieve pain and limited range of motion symptoms from ostheoarthritis that is not relieved by traditional, conservative medical treatment and management. It is also utilized in treating refractory synovitis and determining uncertain etiology. The DNAL procedure has also been found to be an excellent alternative for those patients unable to tolerate the risks of general anesthesia or are unwilling/unable to undergo joint replacement.

Osteoarthritis is a common problem for many middle-aged and elderly people. Osteoarthritis is sometimes referred to as degenerative, or wear-and-tear arthritis, produced by aging. It can also result from a direct injury to the joint. Instability from ligament damage and/or meniscal injuries cause abnormal wear and tear of he cartilage on the knee joint. Not all cases of ostheoarthritis are related to prior injury however. Research has shown that many are prone to develop osteoarthritis and the tendency may be genetic. Obesity is also a contributory factor. The main problem of osteoarthritis is degeneration of the cartilage that covers articulating surfaces of the joint, resulting in areas of the joint where bone rubs against bone creating bone spurs. Generally osteoarthritis develops slowly over several years. The symptoms are mainly pain, swelling, and stiffening of the joint. As the condition worsens or progresses, pain can interfere with simple, daily activities. Traditional conservative methods of medical treatment include taking anti-inflammatory medication and cortisone injections to reduce the swelling and inflammation of the joint and a variety of pain medications to suppress the bodies pain response. Recently, intra-articular injections of hyaluronic acid, a natural substance found in synovial fluid, has been added to the physician's arsenal in fighting the debilitating effects of OA.

Recently arthroscopic surgeries have been performed in the doctor's office to diagnose and treat a variety of symptoms including osteoarthritis, rheumatoid arthritis, crystal-induced arthritis, and pain of unknown etiology. DNAL performed in the physician's office is done under local anesthetic, with the patient awake throughout the procedure. A video monitor is typically used and the patient may observe the procedure if desired. The surgical site is prepared and draped in the appropriate manner and the procedure is performed under sterile conditions. Local anesthesia is injected into the tissue surrounding the surgical site and also into the joint.

The correct placement of an entry port or portal is performed in the usual fashion using the cannula with a sharp trocar inserted to pierce the surface tissue and then a blunt trocar (obturator) to pop through the joint capsule. The blunt obturator is removed from the cannula and the 1.7 mm arthroscope is inserted in its place. Irrigation is performed through the cannula which is connected by tubing to a hanging bag of irrigation solution (sterile saline) under pressure. Infusion of saline is performed until a clear visual field is obtained and is intermittently maintained throughout the procedure.

With the arthroscope inserted in the cannula and a clear field, the compartments of the knee may be visualized and inspected. If biopsy of interarticular tissue is desired or cartilage thickness and quality needs to be evaluated, a biopsy cannula is used to replace the diagnostic cannula and the appropriate instrument used. This is accomplished through the same single port into the joint and under visualization.

The irrigation or lavage of the joint and subsequent aspiration or removal of fluid, removes particulate matter and loose bodies floating in the joint and has been clinically documented in having beneficial effects with regard to pain relief. The flushing of diseased synovial fluid containing irritants, a byproduct of OA, is also therapeutic. By comparison, operative arthroscopy requires a minimum of two larger ports into the joint for biopsy; one for the arthroscope and one for instrumentation. A disadvantage of the present system of operative arthroscopy is the requirement for a second portal for insertion of surgical instruments.

It is therefore one object of the present invention to provide a diagnostic needle arthroscopy and lavage system using a single port entry system allowing the physician to use a minimally invasive, direct visualization approach for diagnosis and also provide therapeutic benefit of complete flushing of the joint with sterile saline (lavage).

Another object of the present invention is to provide a unique proprietary suction/irrigation handpiece that doubles as a diagnostic entry cannula into the joint and also as a housing for a 1.7 mm fiberoptic arthroscope during the procedure. The handpiece also provides suction and irrigation capabilities on demand through finger controlled trumpet valves.

Another object of the present invention is to provide a diagnostic needle arthroscopy and lavage system that permits diagnostic evaluation of a joint along with therapeutic lavage which provides long-term pain reduction/relief by flushing loose bodies and the chemical irritants commonly found in chronic osteoarthritis (OA) and rheumatoid arthritis (RA).

Yet another object of the present invention is to provide a diagnostic needle arthroscopy and lavage system that uses devices of very small size and a single entry port that is an advantage over multiple punctures and larger ports used in standard operative arthroscopy making the procedure ideal for use in a physician's office. With the system disclosed and described, arthroscopic diagnosis and lavage may be performed under local anesthetic only and in conjunction with a mild oral sedative. Patients experience minimum discomfort and generally return to normal activities the next day.

Still another object of the present invention is to provide a diagnostic needle arthroscopy and lavage system as an alternative to magnetic resonance imaging (MRI) for diagnosing joint disease and derangement. The diagnostic needle arthroscopy and lavage procedure is both diagnostic and therapeutic while the MRI is only diagnostic and does not permit the opportunity to visualize joint pathology directly, sample tissue, or allow certain interventional treatment modalities.

Direct visualization of joint surfaces and pathology is a superior form of diagnosis when compared to MRI and is also another object of the invention.

Still another object of the present invention is to provide a diagnostic needle arthroscopy and lavage procedure that allows some patients, particularly the elderly, those with heart disease, compromised respiratory function and diabetics, that are not candidates for traditional operative procedures that have the added risk of general anesthesia, to be treated. The system of the present invention provides those patients who have failed conservative medical management and are unable to undergo total or partial joint replacement, a minimally invasive alternative with a high rate of clinically documented success.

BRIEF DESCRIPTION OF THE INVENTION

The purpose of the present invention is to provide a diagnostic needle arthroscopy and lavage system that permits examination and treatment through a single port entry allowing a physician to use minimally invasive, direct visualization approach for diagnosis.

Suction and irrigation have been standard features in operative arthroscopy (joint), laparoscopy (abdomen/pelvis), cystoscopy (bladder), and hysteroscopy (uterus) for several years. Laparoscopy and hysteroscopy currently use carbon dioxide ($CO_2$) gas as the primary distention media which is electrically monitored and controlled. Hysteroscopy also uses fluid as the distention media, similar to operative arthroscopy and cystoscopy. Operative arthroscopy, hysteroscopy, and cystoscopy primarily use irrigation fluid as distention media only, allowing the specific cavity or organ to be extended or open for viewing and performing operative tasks.

The suction and irrigation aspect in laparoscopy uses fluids in a lavage fashion for flushing the cavity/tissue/organ of blood and debris for better visualization, but the distension of the abdomen is accomplished with $CO_2$ gas. Both arthroscopy and laparoscopy require a sharp puncture through tissue to enter the respective cavity while in hysteroscopy, the entry into the uterus is through the vagina and dilation of the cervix and in cystoscopy through dilation of the urethra. No sharp instruments are used in either for the purpose of cavity entry.

Operative arthroscopy generally has irrigation entering through one port and suction through a second port or through the shaving device introduced through a second port. Hysteroscopy and cystoscopy utilize an outer sheath around the scope which allows the constant inflow and outflow of fluid, preset at specific volume and flow levels and controlled by machine. When fluid is the primary distention media in hysteroscopy, flow can also be controlled intermittently with the use of a physician operated foot pedal.

The diagnostic needle arthroscopy and lavage system of the present invention is distinguished from the usual system and method described above because both inflow and outflow are intermittent and totally physician controlled by trumpet valve buttons on a handpiece. In laparoscopy the inflow and outflow are intermittently controlled via trumpet valve buttons similar to the system disclosed herein, but the suction/irrigation is accomplished through a separate suction/irrigation device introduced through a second port. The device disclosed herein is a suction/irrigation device that combines separate button valves, physician controlled for both suction and irrigation, and doubling as an entry cannula. It is also the only suction/irrigation device that doubles as the scope cannula and permits a single puncture only.

The diagnostic needle arthroscopy and lavage system is particularly adaptable to performing office-based procedures. The single port entry system allows the physician to use minimally invasive direct visualization for diagnosis and also provide therapeutic benefit by completely flushing the joint with sterile saline (lavage). The single port entry is facilitated through a unique disposable suction/irrigation handpiece which doubles as diagnostic entry cannula into the joint and also as the housing for the small fiberoptic arthroscope during the procedure. Separate irrigation and suction capabilities are incorporated in the handpiece and are physician accessed on demand through finger-controlled trumpet valves.

The disposable handpiece's integral suction and irrigation tubing set connects the handpiece to the respective dual canister vacuum pump and dual irrigation pump which is pressure controlled via a separate air compressor. These components are mounted on a portable procedure cart which also contains a video system housing the camera, light source, lensing and focus in a single enclosure. The video system also includes a high-resolution monitor for viewing and a video recording or video printing device for documenting the procedure.

Additional capabilities for biopsy under visualization through the single port are accomplished with a separate, unique biopsy cannula which is exchanged with the diagnostic cannula via an exchange rod. The scope is removed from the handpiece and the exchange rod inserted in its place. The diagnostic cannula and attached suction/irrigation handpiece may then be removed leaving only the exchange rod in the joint. The diagnostic cannula is then unscrewed from the front of the suction irrigation handpiece and the larger diameter biopsy cannula is attached in its place.

Prior to insertion of the biopsy cannula, the tapered dilator shaft is slipped over the exchange rod and inserted into the joint, gently expanding the portal opening to accommodate the larger sized cannula. The tapered dilator shaft is removed and the biopsy cannula and attached suction/irrigation handpiece are then slipped back over the exchange rod and inserted into the joint, eliminating the time-consuming nuisance of finding the original entry path into the joint. The exchange rod may then be removed and replaced with the arthroscope. A 1 mm biopsy forceps is then inserted through the auxiliary valve mounted on the biopsy cannula body allowing for biopsy under direct visualization. Additional 1 mm devices for use through the auxiliary valve of the biopsy cannula permit cutting and shaving/ablation of tissue.

The system disclosed is intended as a diagnostic procedure for joint evaluation while therapeutic lavage provides long-term (6–24 months) pain reduction/relief by flushing out loose bodies and chemical irritants commonly found in chronic osteoarthritis (OA) and rheumatoid arthritis (RA). The small size of the devices (less than half the size of standard, operative arthroscope) and single-entry port rather than multiple punctures and ports in standard operative arthroscopy, make this procedure ideal for a physician's office. The procedure is performed under local anesthetic only and in conjunction with a mild oral sedative (e.g., Valium), eliminating the additional risks and associated complications of general anesthesia or spinal epidural injections. Patients undergoing the procedure experience minimal discomfort and return to normal activities the next day.

At the onset of the procedure a sharp trocar is inserted into the suction/irrigation handpiece and attached diagnostic cannula. The entire device is then inserted into the joint to the level of the joint capsule. The sharp trocar after piercing the surface tissue is replaced with a blunt trocar (obturator) and "popped" into the interior of the joint through the joint capsule. The blunt trocar is removed and replaced with the fiberoptic arthroscope and after attaching the disposable handpiece's integral suction/irrigation tubing set to the respective devices located off the sterile field; irrigation and aspiration of the joint with sterile saline commences.

The joint is alternately irrigated and suctioned until a clear picture is obtained, the diagnosis is performed while continuing to flush as needed to maintain a clear operative field and to wash out loose bodies and irritants contained within the joint. Generally 1 to 3 liters of saline are used to perform the lavage and to clean the joint of loose debris. Should a biopsy be desired, the procedure for exchanging diagnostic and biopsy cannula can be used.

The diagnostic and biopsy cannula are attached to a threaded coupling or fixture that includes a stopcock or ball valve that allows for removal of sterile synovial fluid and loose bodies, and also permits direct injection of anesthetic or drugs, into the joint. In addition, the biopsy cannula's ball valve is also used for insertion and removal of the biopsy instrument. The invention disclosed herein is the only application of an additional valve on the suction/irrigation device which is different from the large number of standard entry trocar/cannula that utilize a valve for distention purposes only.

The system also includes the use of video coupling optics connected to the camera head, and light source in a single unit located off the sterile field. This eliminates the need to have a camera head and cable, optical coupler, light cable and scope all sterilized and assembled on the field. The only video train component in this system disclosed herein needing sterilization is the fiberoptic scope which contains integral illumination fibers. The 1.7 mm scope in this system uses a 30,000 pixel fiber image bundle with a two-element distal lens which provides the image quality, large field of view, and depth of field approaching that of a 4 mm rod lens arthroscope.

Other objects, advantages, and novel features of the invention will become apparent from the following detailed description when considered in conjunction with the accompanying drawings where in like reference numbers and identifying light parts throughout.

DETAILED DESCRIPTION OF THE INVENTION

Figures 1, 2:
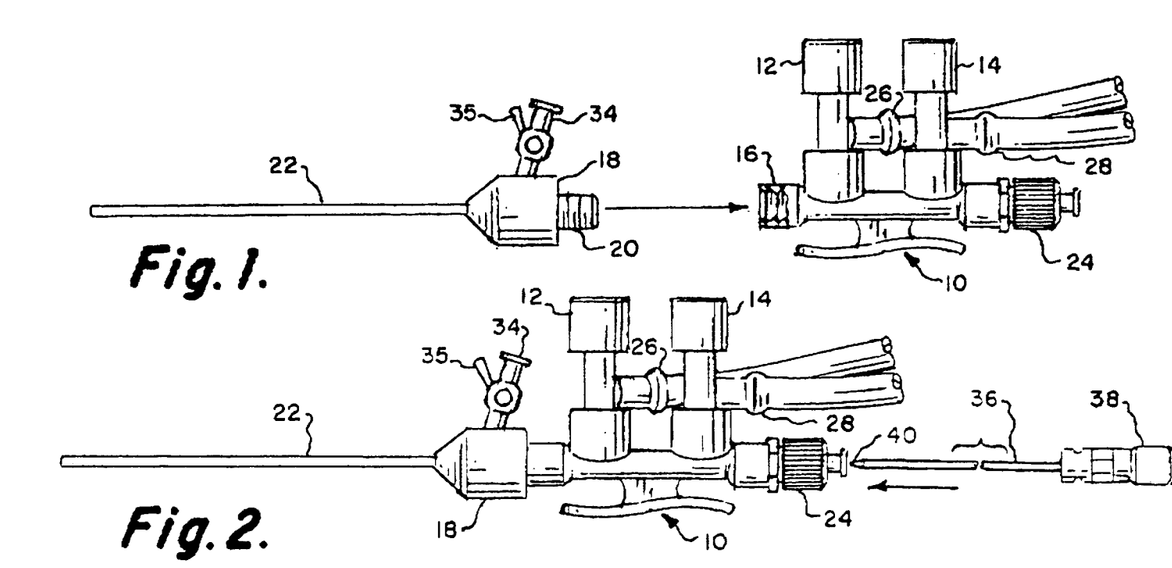
FIG. 1 is a plan view of a handpiece for use in diagnostic needle arthroscopy and lavage system illustrating the connection of the diagnostic cannula.
FIG. 2 is a plan view illustrating the insertion of a sharp trocar through a disposable handpiece and diagnostic cannula for piercing the skin and surface tissue directly above the joint being entered.

The diagnostic procedure components of the system are illustrated in FIG. 1 and are comprised of a handpiece 10 having trumpet valves 12 and 14 and threaded socket 16 for receiving coupling 18 having threaded nipple 20 and a diagnostic cannula 22. Threaded nipple 20 is threaded into socket 16 in handpiece 10 to secure diagnostic cannula 22 to handpiece 10. Fitting 24 on the opposite end of handpiece 10 receives instruments to pass through handpiece 10, coupling 18 and diagnostic cannula 22 as shown in FIGS. 2 through 10. Handpiece 10 also has irrigation and suction tubes 58 and 66 attached to trumpet valves 12 and 14 through channels 26 and 28. A unique feature of the invention is the inclusion of an auxiliary stopcock or ball valve 34 attached to coupling 18 which may be used for direct medication into the joint and/or sterile synovial fluid removal which will be described in greater detail hereinafter.

Figures 3, 4:
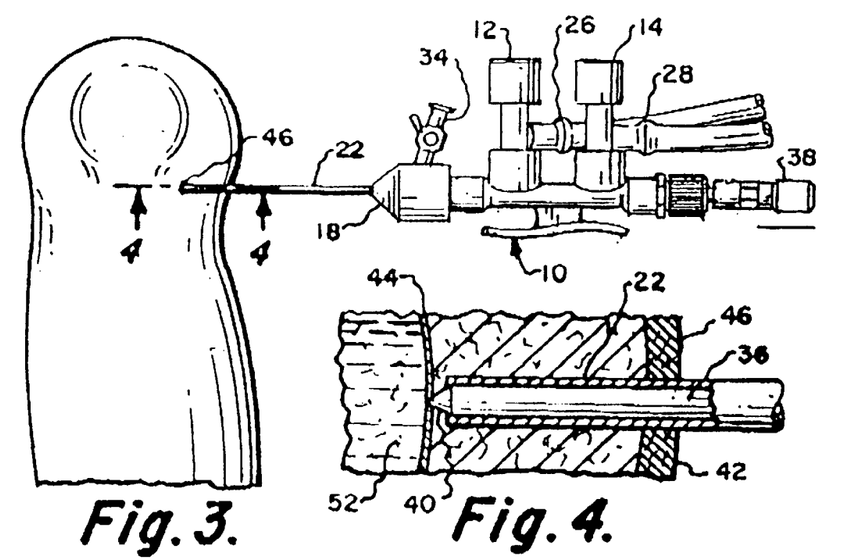
FIG. 3 is a plan view illustrating the insertion of the handpiece with a trocar through the surface tissue of the knee joint with the sharp trocar locked in place and penetrating the tissue to the depth of the joint capsule.
FIG. 4 is a partial sectional view taken at 4—4 illustrating the sharp trocar locked in place in the diagnostic cannula piercing the surface tissue.

The placement of the diagnostic cannula of the DNAL system is illustrated in FIGS. 2 through 7. Initially an introducer in the form of a sharp trocar 36 having handle 38 is inserted into fitting 24 in handpiece 10 and passed through channel 15 (FIG. 12B) into cannula until the sharp tip 40 extends out of diagnostic cannula 22 as illustrated in FIG. 4. Sharp trocar 36 is used to pierce the skin 42 and surface tissue directly above the joint at the point of insertion until it reaches the joint capsule 44, creating entry portal 46.

Figures 6, 7:
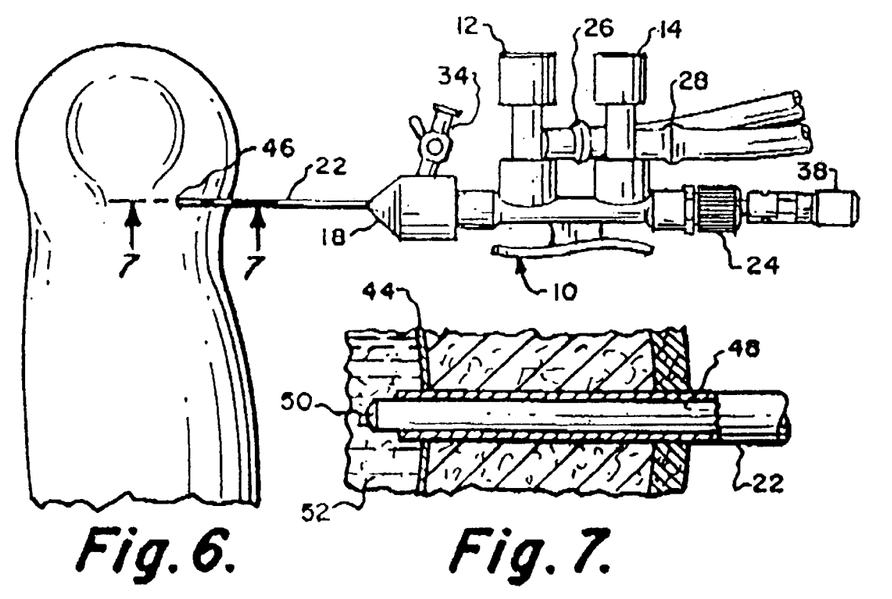
FIG. 6 illustrates the insertion and locking in place of the obturator through the diagnostic cannula.
FIG. 7 is a partial section illustrating the obturator in the diagnostic cannula penetrating the joint capsule and inside the joint space.

FIG. 3 illustrates placement of the diagnostic needle arthroscopy and lavage system in a knee joint but, of course, the system may be used for other joints as well. After diagnostic cannula 22 with sharp trocar 36 reaches joint capsule 44, sharp trocar 36 is withdrawn and replaced with blunt obturator 48 having a blunt end 50. Blunt obturator 48 is passed through fitting 24 in handpiece 10 and diagnostic cannula 22 as shown in FIGS. 6 and 7. With diagnostic cannula 22 in portal 46, blunt trocar 48 pushed (i.e. "popped") through joint capsule 44 into interior joint space 52. Diagnostic cannula 22 is now positioned in interior joint space 52 ready for use in examining the joint.

Figure 5:
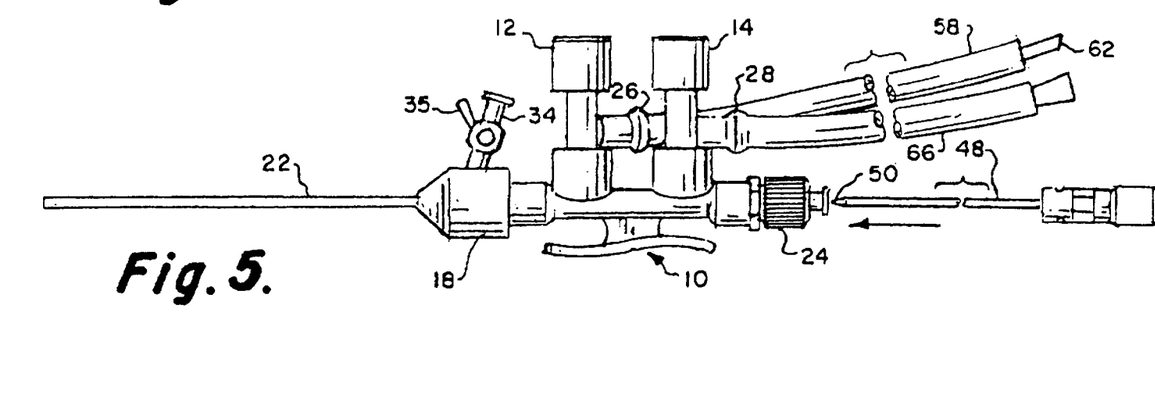
FIG. 5 is a plan view illustrating the replacement of the sharp trocar with the blunt trocar (obturator) for puncturing the joint capsule.
Figures 8, 9, 10, 11:
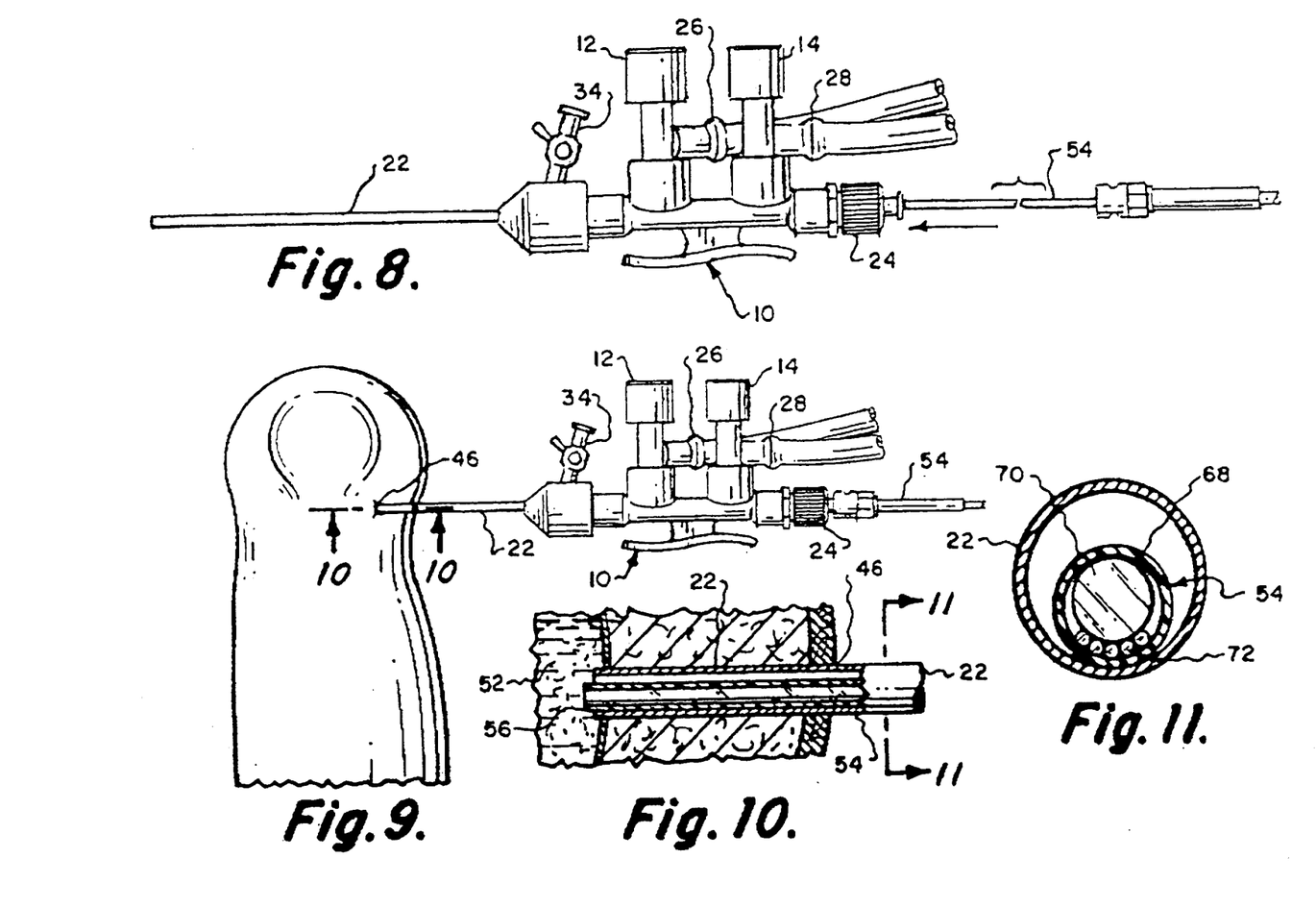
FIG. 8 is a plan view of the diagnostic needle arthroscopy and lavage disposable handpiece with the diagnostic cannula attached illustrating insertion of the arthroscope.
FIG. 9 illustrates the diagnostic cannula in the knee joint with the arthroscope locked in position.
FIG. 10 is a sectional view taken at 10—10 of FIG. 9 illustrating the diagnostic cannula in the joint and the arthroscope extending slightly beyond the end of the cannula.
FIG. 11 is a sectional view taken at 11—11 illustrating the distal, circumferential structure of the diagnostic cannula and arthroscope. The distal optics of the arthroscope are also illustrated.

An arthroscope 54 is then inserted through and locked into fitting 24 in handpiece 10 into diagnostic cannula 22 and extends slightly beyond the distal end of diagnostic cannula as illustrated in FIG. 10. The entire diagnostic cannula 22 may now be extended through portal 46 deep into joint compartment 52 with fiberoptic arthroscope extended at 56 to view and inspect all compartments such as the superpatella pouch, patellofemoral joint space, medial recess, medial compartment, intercondylar notch, lateral compartment, and lateral recess. During the inspection and examination, the joint is distended by injecting an irrigation solution through hose 58 (FIG. 5). The irrigation hose 58 has spike 62 for puncturing a seal on irrigation solution (sterile saline) bags (not shown). Irrigation solution is released through irrigation and suction handpiece 10 by operation of trumpet valve 12. The irrigation fluid distends joint space 52 allowing visualization of the interior of the joint.

Direct insertion of medication into the interior joint space and/or removal of sterile synovial fluid may be performed through auxiliary ball valve 34. Medication is inserted by opening auxiliary ball valve 34 by rotating handle 35 providing an entry/exit path through fitting or coupling 18 into diagnostic cannula 22. Medication can then be injected through ball valve 34 into the interior joint space 52. Alternatively, an empty, sterile syringe can be attached to the end of ball valve 34 for removal of sterile synovial fluid for analysis.

The diagnostic procedure is performed by visualizing the interior joint space 52 through arthroscope 54 while irrigating the joint cavity with sterile saline solution through irrigation tubing 58, connected through irrigation 26 by operating trumpet valve 12 to distend the joint. This fills and distends the joint allowing visualization of interior joint space 52 through fiberoptic arthroscope 54. Distal end 56 of arthroscope 54, locked in position in handpiece 10, may be manipulated by moving handpiece 10 around to visualize the inside of interior joint space 52.

After irrigation and distention, suction may be applied by operating trumpet valve 14, through suction channel 28 connected to suction tube 66 (FIG. 5) flowing to dual suction collection canister as will be described in greater detail hereinafter. The irrigation and suction system is used to remove loose bodies, debris and other irritants contained within a diseased joints interior joint space 52. Removal of loose bodies, debris and irritants is found to be beneficial particularly to those suffering from osteoarthritis.

Arthroscope 54 is a small (approximately 1.7 mm) stainless steel sheath 68 (FIG. 11) preferably containing a 30,000 pixel fiberoptic image bundle and having a distal glass lens 70 for viewing the interior of joint space 52 with a CCD camera. Illumination fibers 72 contained in sheath 68 are provided for illuminating joint space 52 with high-intensity light. The outside diameter of fiberoptic arthroscope 54 is approximately ½ the inside diameter of diagnostic cannula 22. This allows larger pieces of cartilage or debris in joint space 52 to be suctioned out through cannula 22 without removing fiberoptic arthroscope 54.

Figures 12A, 12B:
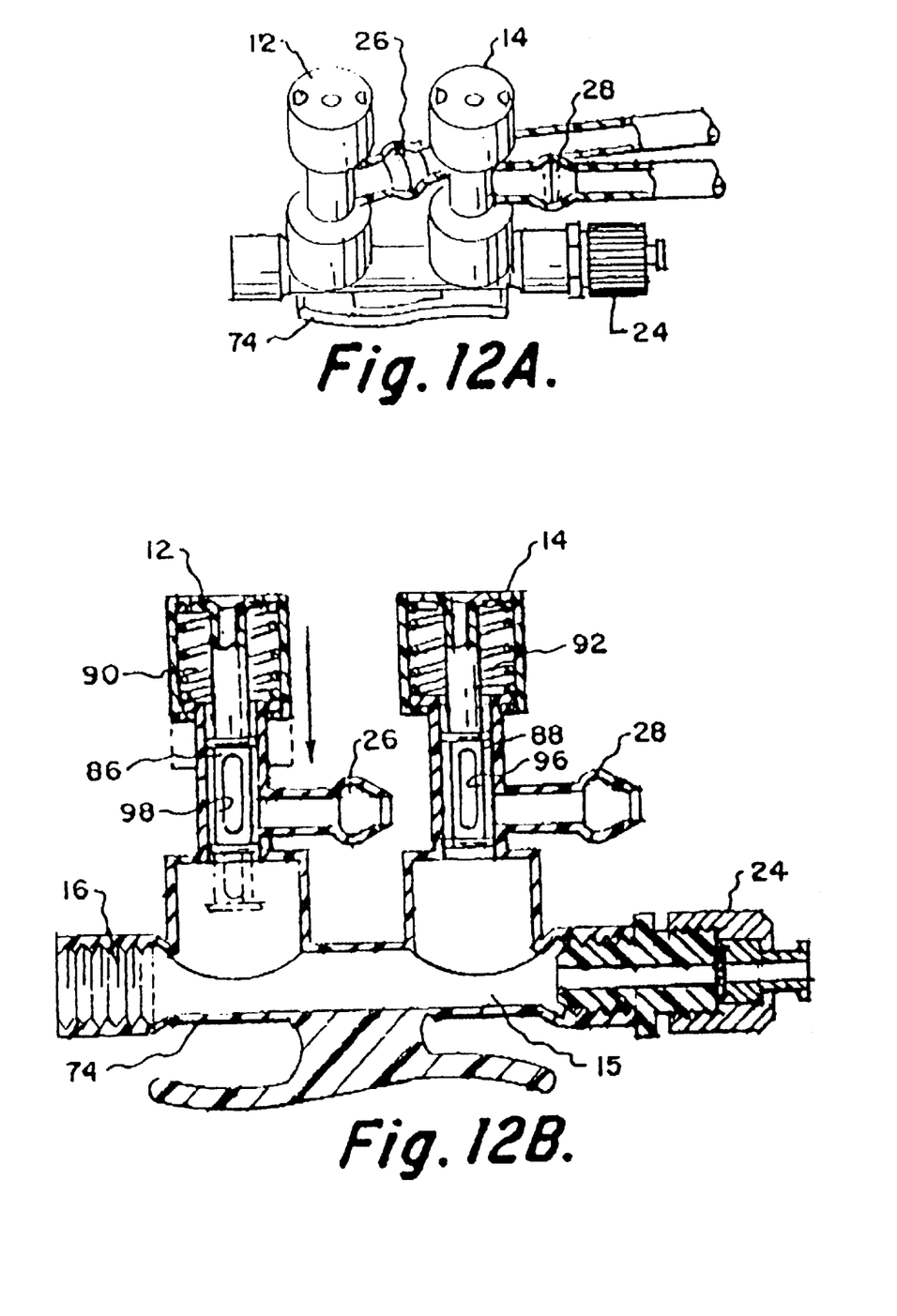
FIG. 12(A) is a combination top/side view showing the orientation of the irrigation and suction valves and integral tubing.
FIG. 12(B) is a cross-sectional view of the disposable handpiece of FIG. 12(A) illustrating the operation of the irrigation and suction valves and their respective flow channels.

The details of the irrigation, suctioning, and manipulating handpiece 10 are illustrated in FIGS. 12(A) and 12(B). FIG. 12(A) is a top/side view illustrating the orientation of trumpet valves 12 and 14 in handpiece 10. Trumpet valves 12 and 14 are in line, with channels 26 and 28, and tubes 58 and 66 slightly offset from each other. This ergonomic arrangement permits handpiece 10 to fit comfortably in the hand of a physician with the index and middle fingers conveniently resting on trumpet valves 12 and 14.

As shown in FIGS. 12(A) and 12(B) irrigation and suctioning handpiece 10 is comprised of a main housing 74, preferably made of molded plastic or aluminum, having an interior passageway 15 connecting fitting 24 with threaded socket 16. Irrigation and suction channels 26 and 28 respectively (FIGS. 12(A),(B)) are connected directly to trumpet valves 12 and 14 to control the flow of irrigation and suctioned fluids through diagnostic cannula 22.

Trumpet valves 12 and 14 are comprised of stems 86 and 88 biased by springs 90 and 92 located at the top of each valve, into a normally closed position. Pressing down on either of trumpet valves 12 and 14 connects passageway 15 through valve stems 86 or 88 to either of channels 26 and 28. This construction allows the physician to manipulate the diagnostic cannula 22 by moving handpiece 10 around and injecting irrigating saline into, or suctioning fluid from joint space 52 as desired.

Irrigating fluid is supplied by pressing trumpet valve 12 to connect interior passageway 98 in valve stem 86 to channel 26. This allows irrigating fluid to flow from irrigating channel 26 into diagnostic cannula 22 through main passageway 15. Suction is provided in the same manner with irrigation trumpet valve 12 in the up, or closed position.

When suction trumpet valve 14 is depressed, channel 28 is connected through passageway 96 in valve stem 88 to main passageway 15. This allows material to be suctioned from joint space 52 through handpiece 10 to collecting canisters as will be described in greater detail hereinafter. Thus the unique construction of irrigating and suction handpiece 10 allows the physician to visualize the interior of joint space 52 while irrigating and suctioning alternately as desired.

Figures 13, 14:
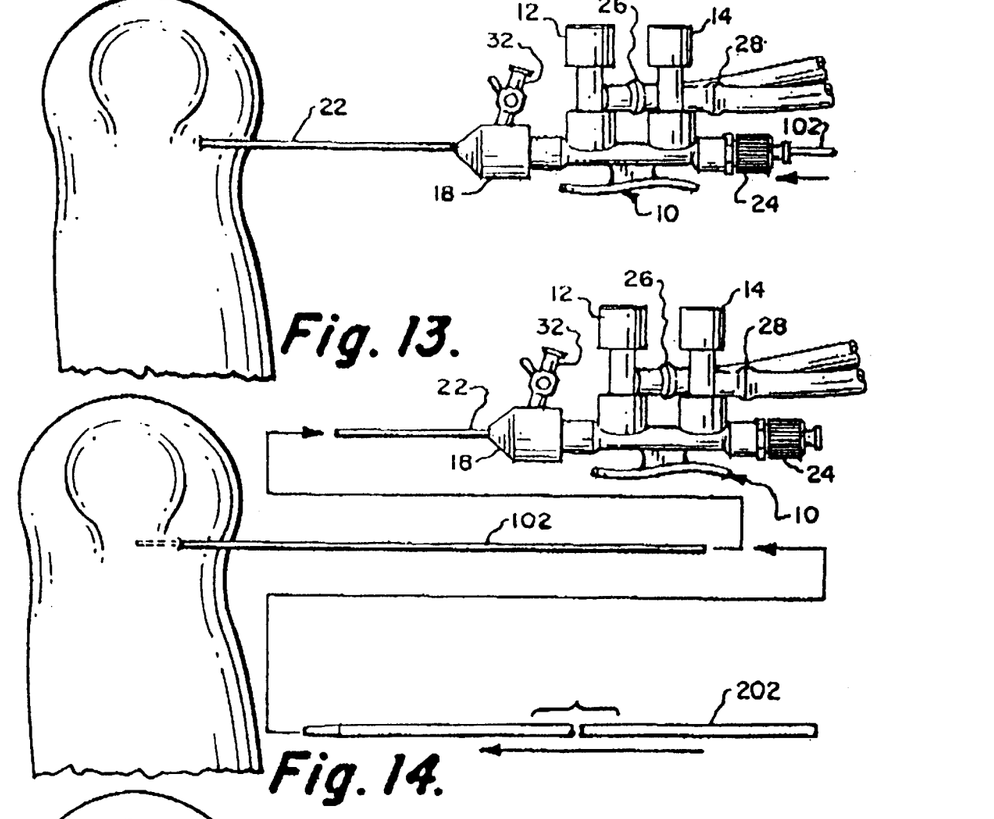
FIG. 13 is a plan view illustrating the insertion of an exchange rod for removing and exchanging the diagnostic cannula.
FIG. 14 illustrates the removal of the diagnostic cannula and replacement with the dilator shaft using the exchange rod.
Figure 15:
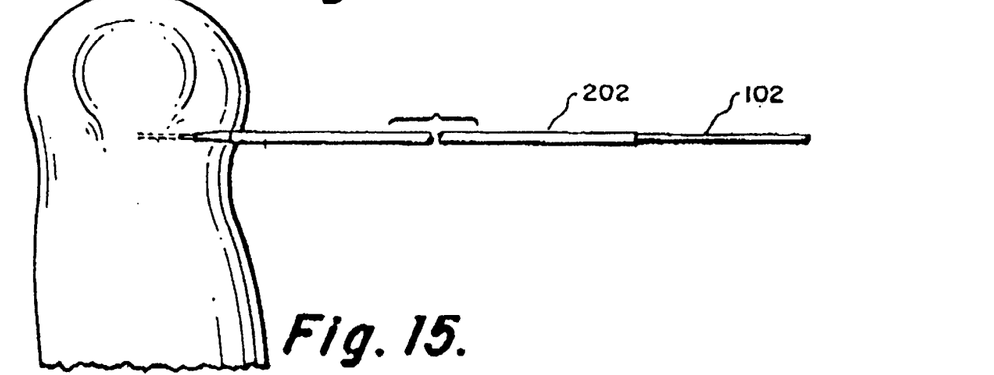
FIG. 15 is a plan view showing the tapered dilator shaft over the exchange rod and inserted in the joint.
Figure 16:
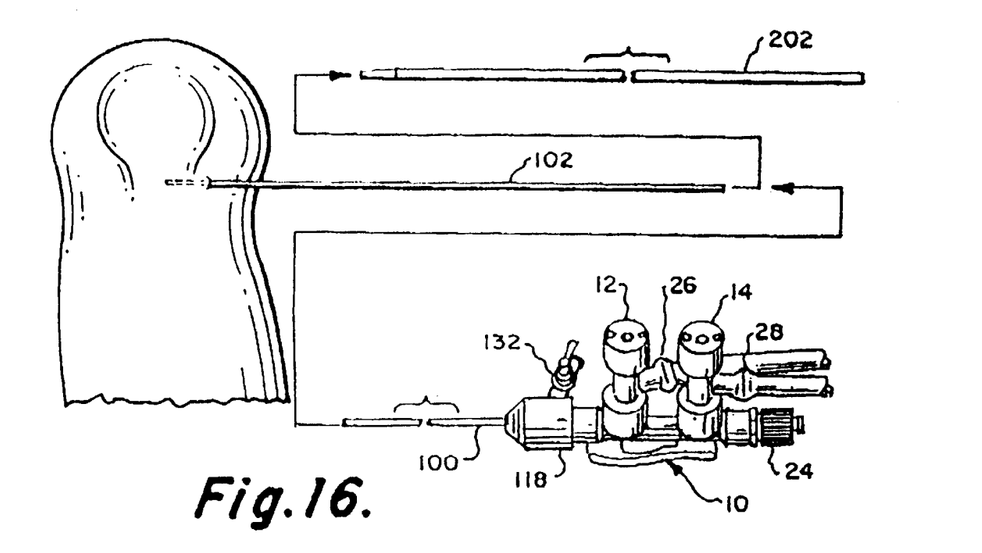
FIG. 16 illustrates removal of the tapered dilator shaft and placement of the biopsy cannula over the exchange rod and into the joint.

Another unique aspect of the invention is the ability to perform biopsies and other surgical functions through irrigating and suctioning handpiece 10 by exchanging the diagnostic cannula 22 for a biopsy cannula 100 as shown in FIGS. 13 through 16. This procedure is facilitated by use of an exchange rod 102 that is passed down through fitting 24 on handpiece 10 though diagnostic cannula 22 until it is inside knee joint space 52. Diagnostic cannula 22 may then be withdrawn with handpiece 10 as shown in FIG. 14. Diagnostic cannula 22 may then be removed by detaching coupling 18 from handpiece 10 as illustrated in FIG. 1.

Figure 17:
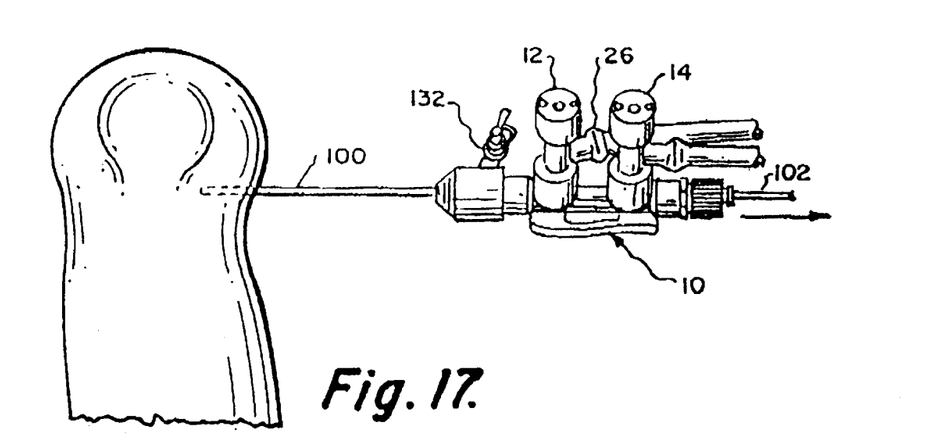
FIG. 17 illustrates the removal of the exchange rod after placement of the biopsy cannula into the joint.
Figures 18, 19:
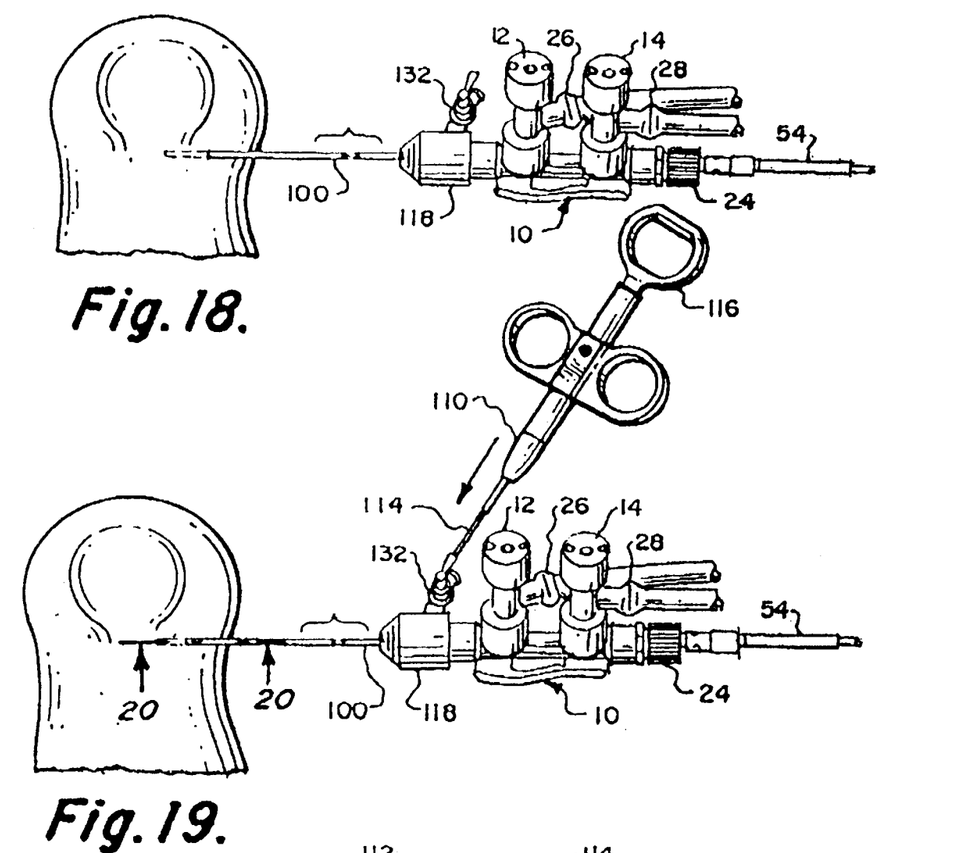
FIG. 18 illustrates placement of the arthroscope into and through the biopsy cannula.
FIG. 19 illustrates the insertion of the 1 mm biopsy instrument through an auxiliary valve on the biopsy cannula.
Figure 20:
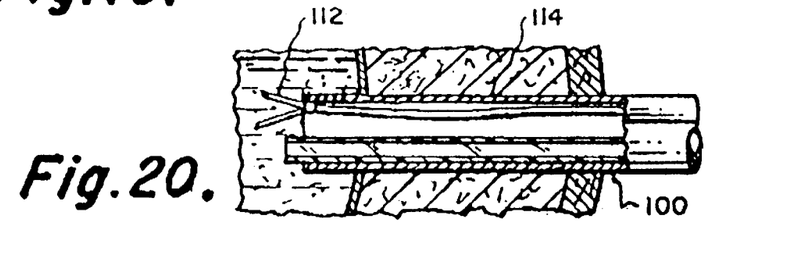
FIG. 20 is a sectional view illustrating the biopsy cannula with biopsy instrument and arthroscope in place inside the joint capsule.

Biopsy cannula 100 is then attached to handpiece 10 by coupling 118 which also has integral stopcock or ball valve 132 for addition of internal joint medication with a syringe, removal of sterile synovial fluid if desired, or insertion of biopsy instrument 100. Tapered dilator shaft 202 is then fed over exchange rod 102 into joint space 52, gently expanding entry portal 46. Upon removal of tapered dilator shaft 102, biopsy cannula 100 is then fed over exchange rod 102 into joint space 52 and exchange rod 102 withdrawn as illustrated in FIG. 17 leaving biopsy cannula 100 in place. Biopsy cannula 100 may now be used for performing surgical procedures, under visualization, such as biopsies as illustrated in FIGS. 19 and 20.

With biopsy cannula 100 in place, arthroscope 54 is inserted through fitting 24 of handpiece 10 into the joint space 52 as before. As can be seen more clearly in FIG. 20, biopsy cannula 100 is comprised of a larger central lumen and angled valve. The lumen of Biopsy cannula 100 allows visualization, suction and irrigation and also tissue biopsy to be performed. Biopsy cannula ball valve 132 also receives a surgical tool or instrument 110 such as biopsy forceps. Forcep jaws 112 at the distal end of flexible shaft 114 connected to surgical instrument 110 is operated by manipulating ring handle 116. Forcep jaws 112 can be used to break up larger pieces of debris that might not fit through the cannula lumen or can be used to bite and remove tissue specimens from interior joint space 52.

Biopsy cannula 100 is used to perform biopsies with a biopsy forcep of approximately 1 mm in size being inserted through ball valve 132 allowing biopsies to be performed under direct visualization through arthroscope 54. Additional 1 mm devices for performing the tasks of cutting, shaving and ablation through ball valve 32 will also be available. The use of exchange rod 102 and tapered dilator shaft 202 eliminates the time-consuming nuisance of finding and gently enlarging original entry path 46 into interior joint space 52 adding an additional level of safety by eliminating the need to create a new entry path with the sharp trocar. While the system is described as performing an irrigation and lavage first and biopsy second, of course, the steps could be reversed or one used without the other. That is, the system can be used for a biopsy first followed by an irrigation and lavage or could be used to perform a biopsy or an irrigation and lavage separately, if desired.

The diagnostic system allows alternate irrigation and suctioning until a clear picture is obtained through the arthroscope and displayed on a monitor as will be described hereinafter. While examination and diagnosis are performed, intermittent flushing is needed to maintain a clear operative field and to wash out loose bodies and irritants contained within the interior joint space 52. Generally up to 3 liters of sterile saline are used to perform the lavage and flush joint space 52. Should a biopsy be desired, the procedure for exchanging diagnostic and biopsy cannula as described hereinabove is employed.

Both inflow and outflow are intermittent and totally physician controlled via trumpet valve buttons 12 and 14 on irrigation and suctioning handpiece. The separate irrigation and suctioning capability incorporated in handpiece 10 are very efficient as they are physician accessed on demand through the finger control trumpet valve while manipulating handpiece 10. In prior art devices and surgical procedures such as in laparoscopy, the inflow and outflow by irrigation and suctioning is accomplished through separate suction and irrigation devices introduced through a second port. With the device disclosed herein, the suction and irrigation is both the distention media and also the primary therapy. The device is unique as it combines a separate physician controlled button valve for both irrigation and suction while doubling as an entry cannula and a scope cannula and permits a single puncture or port entry.

The use of the auxiliary stopcock or ball valve on the front coupling of the diagnostic and biopsy cannulas allow for removal of sterile synovial fluid and loose bodies and direct injection of anesthetic and medication into the interior joint space 52, and also allows for instrument insertion and specimen removal when using biopsy cannula 100. The inclusion of the stopcock and ball valve allows for the unique function of uninterrupted irrigation and suctioning on a larger scale, while also allowing addition of anesthetics on both diagnostic cannula 22 and biopsy cannula 100 and removal of sterile biopsy specimens/tissue through valve 132 located on biopsy cannula 100.

In the embodiment of FIG. 19, diagnostic cannula body 22 is elongated by coupling 118 containing an angled or curved channel terminating in stopcock valve 132 that allows arthroscope 54 to stay in the joint and maintain its position while simultaneously inserting biopsy instrument 110 through curved stopcock valve 132 and into the cannula central lumen when required. This embodiment is illustrated by stopcock valve 132 integrally formed on elongated fitting 118 which is part of the diagnostic cannula body. A curved or angled channel through fitting 118 into the cannula allows the arthroscope to remain in place when inserting a biopsy instrument through stopcock valve 132.

Figures 19A, 19B, 19C:
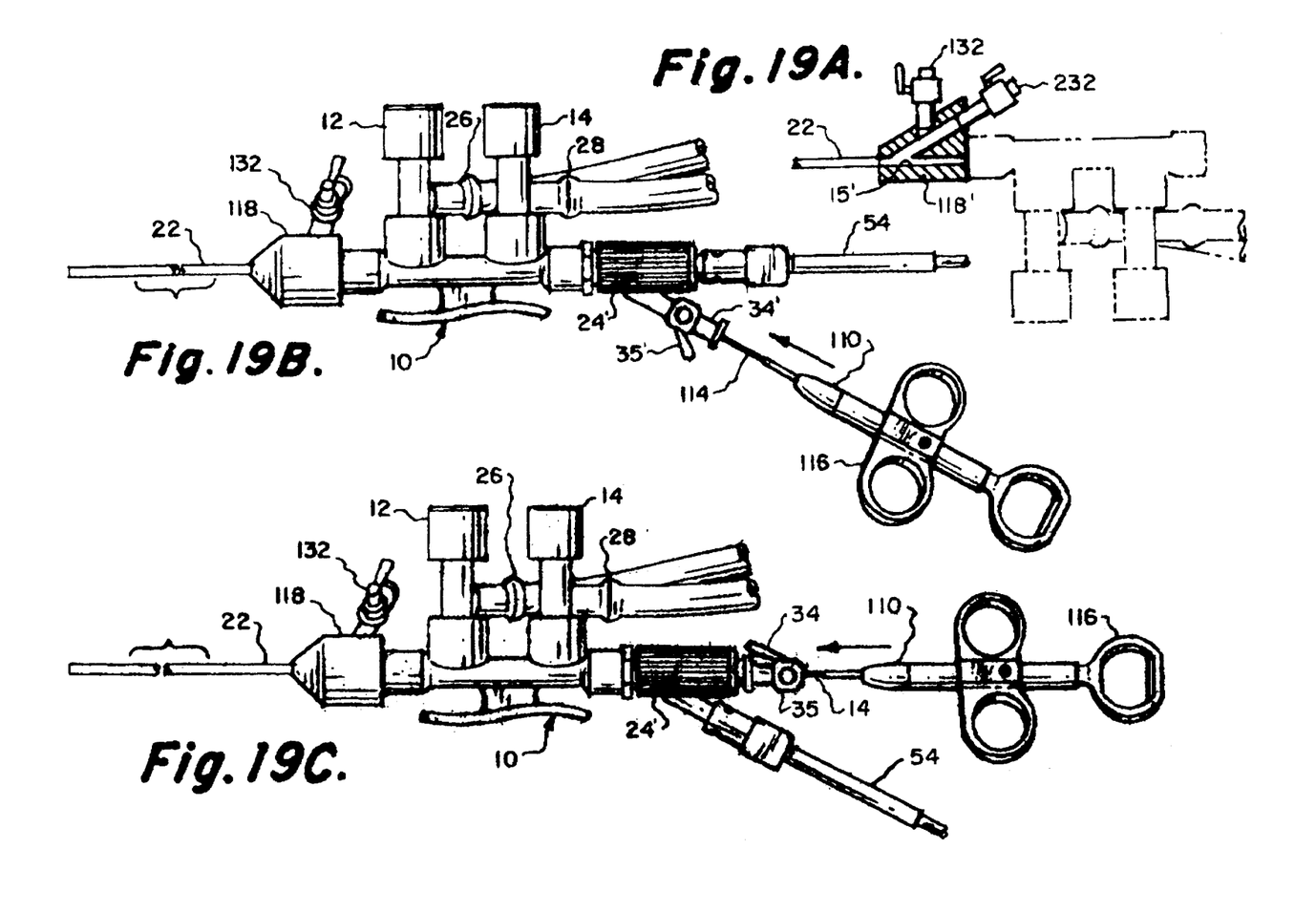
FIG. 19A illustrates a variation of the optional embodiment of FIG. 19. That allows insertion of a biopsy instrument through an auxiliary valve at the rear of a cannula body and eliminates the requirement for an exchange to a second, larger diameter cannula.
FIG. 19B illustrates an optional arrangement for insertion of a biopsy instrument through an auxiliary valve on the rear of the handpiece.
FIG. 19C illustrates a variation of the optional embodiment of FIG. 19B.

Optional embodiments for simultaneous biopsy while under direct visualization through a single port that eliminate the need for exchanging to second, larger cannulas are illustrated in FIGS. 19A, 19B, and 19C. In the embodiment of FIG. 19A, cannula body or fitting 118' contains two separate stopcock valves communicating with internal channels 15' and 115 contained within body 118'. Valve 132 is used exclusively for removal of sterile fluid and loose bodies, or infusion of medication through channel through channel 115. Valve 232 at the rear of channel 115 is used exclusively for insertion and removal of biopsy instrument 110, eliminating the need to exchange cannula and also eliminating the need to exchange the biopsy instrument for a syringe if/when intra-articular medication is desired. This allows arthroscope 54 to stay in the joint while simultaneously inserting biopsy instrument 110 through stopcock valve 232 and into the cannula central lumen when required.

Another optional but preferred embodiment for simultaneous biopsy under direct visualization through a single port illustrated in FIG. 19B also eliminates the need for exchanging cannulas. An elongated "Y" or offset "V" type coupling or connector 24' at the rear of disposable handpiece 10 allows arthroscope 54 to remain in the joint and maintain its position in one channel of the "Y" while a 1 mm biopsy instrument 110 is inserted through the other "Y" channel when required. In this embodiment valve 34' has stopcock 35' and receives biopsy instrument 110 through valve 34'.

Another alternative to the optional embodiment of FIG. 19B is illustrated in FIG. 19C. This embodiment also makes use of the "Y" or offset coupling on rear connector 24' containing two channels. However the coupling is constructed to allow the transposition of arthroscope 54 and biopsy instrument 110 illustrated in the embodiment of FIG. 19B.

Figure 21:
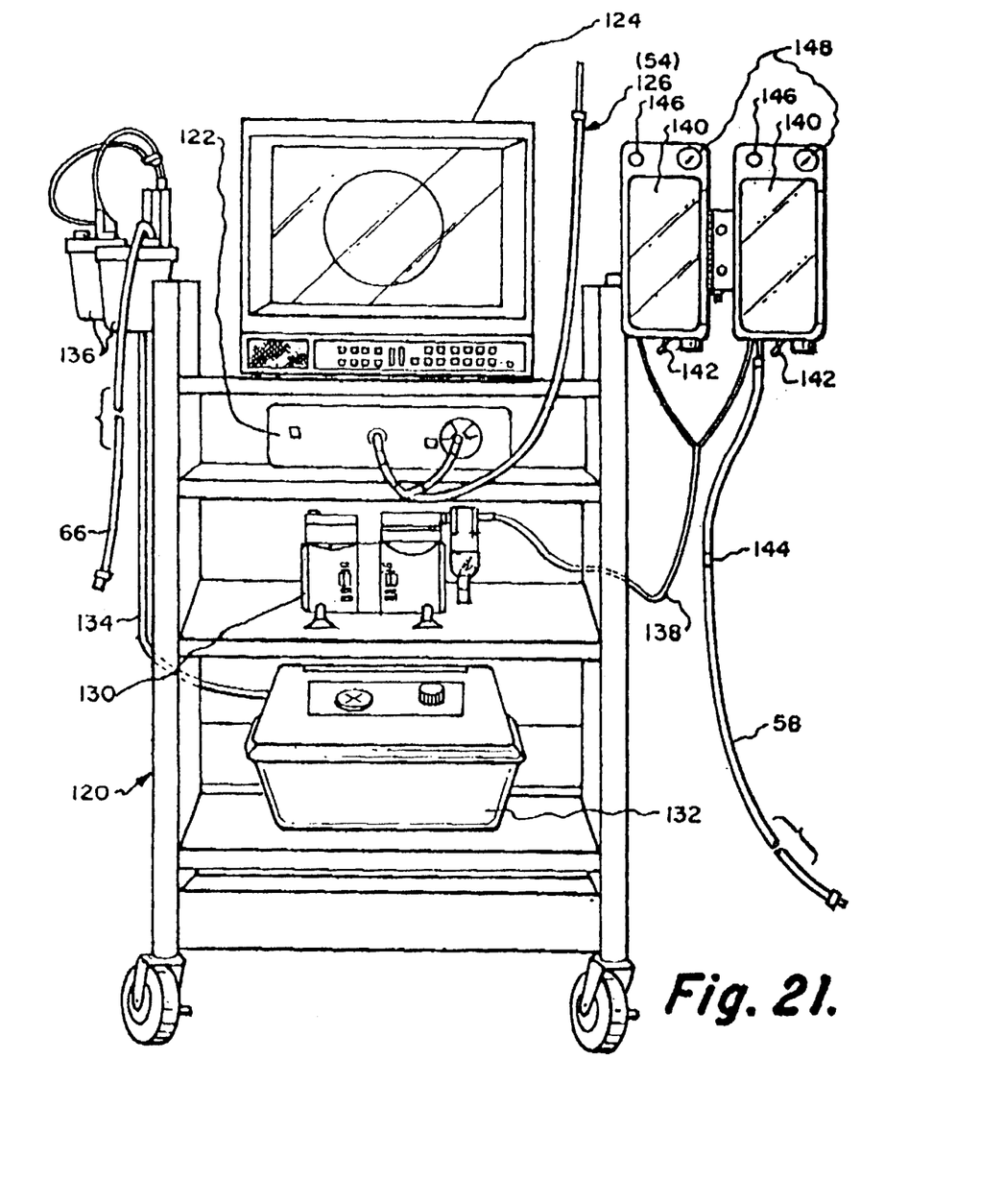
FIG. 21 illustrates the DNAL procedure cart housing the video monitor, camera, light source, optical coupler and focus mechanism, video recording device (not shown), air compressor and dual irrigation pump, suction unit and dual collection canisters with suction and irrigation tubing attached and proximal arthroscope inserted into the separate optical and illumination receptacles on the front of the video system.

The entire operating system for visualization, irrigation, and suction and biopsy as well as documenting the procedure is mounted on a mobile self-contained cart for ease of movement and storage with a small footprint for use in a confined office environment. The support system for the diagnostic needle arthroscopy and lavage system is illustrated in FIG. 21. Portable cart 120 has shelves for receiving the components that work with the diagnostic system shown in FIGS. 1 through 20. A CCD camera, camera head, light source, optical coupling lens and focusing mechanism are all contained within console 122 which is mounted on the next to the top shelf of portable cart 120 along with a high-resolution monitor 124 mounted on the top shelf. Console 122 is directly connected to arthroscope 54, 126 in FIG. 21, having distal lens 70 and light conducting fibers 72 as illustrated in FIG. 11.

A video recording device (not shown) is provided for recording and documenting the procedure. Irrigation pressure is provided by air compressor 130 and controlled by irrigation pumps 140. Vacuum suction is controlled by console pump 132. Vacuum suction console is connected by a vacuum pipe 134 to collection canisters 136 mounted on the side of cart 120. Collection canisters 136 are connected to suction channel 28 on handpiece 10 by suction hose 66 as shown in FIG. 5.

Compressor 130 provides forced air through tubing 138 to dual irrigation pumps 140 each pressurizing 1 liter bags of sterile saline. Sterile saline bags are connected to irrigation channel 26 on handpiece 10 by irrigation hose 58 with integral bag spike 62. Irrigation pumps 140 each have a switch 142 for selecting one or the other of the pumps to be pressurized. This allows empty saline solution in one pump to be replaced while the flow is being delivered from the other pump. Separate pressure controls 146 and pressure gauges 148 are contained on pumps 140 for safe, accurate pressure control. Clamp 144 on irrigation hose 58 also closes to prevent premature flow of solution to suction irrigation handpiece 10.

A unique advantage of this system and its concept is the optical coupler, focusing mechanism, CCD camera, camera head and light source are all contained in one unit located away from the sterile field. Additionally, the need for a separate light cable is also eliminated. The only optical/visualization component requiring sterilization is the arthroscope (54, 126 in FIG. 21). Other components of the DNAL system used within the sterile field are the disposable irrigation and suctioning hoses 58 and 66, handpiece 10, diagnostic and biopsy cannulas 22 and 100 along with sharp trocar 36, blunt obturator 48, exchange rod 102, dilator shaft 202 and biopsy instrument 110.

To perform the DNAL procedure, diagnostic cannula 22 is placed in interior joint space 52 as illustrated in FIGS. 1 through 7. Irrigation and suctioning hoses 58 and 66 are permanently connected to irrigation and suction channels 26 and 28 on handpiece 10 and fiberoptic arthroscope 54 inserted through diagnostic cannula 22. Alternately irrigation and suction is provided until a clear picture is obtained on monitor 124. Examination and diagnosis is performed while continuing to flush as needed by manipulating irrigation and suction trumpet valves 12 and 14 to maintain a clear operative field. Suctioning trumpet valve 14 is operated to flush out loose bodies and debris as well as irritants contained in joint space 52.

Generally up to 3 liters of sterile saline are used to perform the lavage and clean interior joint space 52. Biopsies and limited surgical procedures can then be performed by exchanging diagnostic cannula 22 for biopsy cannula 100 as illustrated in FIGS. 13 through 20. With arthroscope 54 in place through biopsy cannula 100, a surgical instrument approximately 1 mm in diameter may be passed through valve 132 to perform minor biopsies with forcep jaws 112. Cutting, shaving and ablation applications will also be accomplished through valve 132. The embodiments of FIGS. 19A through 19C permit irrigation, suction and biopsy under direct visualization while eliminating the need to exchange to a second, larger cannula which saves time and the inconvenience of relocating the desired specimen site. The entire procedure is performed using only a single, small entry port which minimizes trauma to the patient. The single puncture wound is dressed and covered with a simple bandage.

Thus there has been disclosed a unique and novel diagnostic needle arthroscopy and lavage system that uses only a single point of entry for performing diagnostic and therapeutic procedures. The system includes a handpiece having valves for simultaneously manipulating a diagnostic or biopsy cannula while performing irrigation and suctioning to wash out and remove any debris, loose bodies, as well as irritants contained within the joint. The system also includes a biopsy cannula that can be easily exchanged by use of an exchange rod and dilator shaft. The biopsy cannula also allows for both irrigation and suction as well as biopsies to be performed with a biopsy instrument inserted through the auxiliary ball valve. In addition, both diagnostic and biopsy cannulas have the ability to separately infuse medication and remove sterile synovial fluid through the additional stopcock valve located on couplings 18 and 118.

This invention is not to be limited by the embodiment shown in the drawings and described in the description which is given by way of example and not of limitation, but only in accordance with the scope of the appended claims.

What is claimed is:

1. A multi-function diagnostic needle arthroscopy and lavage system for diagnostic examination and therapeutic treatment of joint diseases permitting entry, visualization, irrigation, suction, and biopsies through a single, small portal comprising;
    a handpiece having a central passageway;
    irrigation and suction channels connected to said handpiece;
    irrigation and suction valves in said disposable handpiece for intermittent control of irrigation fluid and suctioning;
    a cannula;
    a coupling for attaching said cannula to said handpiece;
    instruments for inserting said cannula attached to said disposable handpiece into said joint;
    a fiberoptic arthroscope for insertion through said handpiece and said cannula after removal of said instruments for visualization of the interior joint space, examination, and diagnosis;
    said handpiece constructed for manipulating said diagnostic cannula in a joint space while alternately irrigating and suctioning by operation of said irrigation and suction valves;
    whereby said joint may be efficiently and conveniently examined, diagnosed, and treated through a small single entry port, permitting the use of local anesthetic only.

2. The system according to claim 1 in which said handpiece is a disposable handpiece.

3. The system according to claim 1 in which said irrigation and suction valves are trumpet valves in communication with a central passageway through said disposable handpiece.

4. The system according to claim 1 including an auxiliary valve in said coupling providing access to said space through said cannula.

5. The system according to claim 1 in which said arthroscope, with integrated illumination fibers is directly connected to an optical coupler, camera head, CCD camera, and light source; said arthroscope having an outside working diameter that is equal to or less than approximately one-half the inside diameter of said cannula.

6. The system according to claim 5 in which said coupling for attaching said cannula to said handpiece is a coupling with said cannula attached; said handpiece having a socket for receiving said coupling whereby said cannula may be quickly attached or removed from said disposable handpiece.

7. The system according to claim 6 in which said cannula is a biopsy cannula.

8. The system according to claim 7 in which said instruments comprise a sharp trocar and blunt obturator for inserting said cannula into said joint space.

9. The system according to claim 8 in which said cannula is a biopsy cannula that is exchanged by use of an exchange rod.

10. The system according to claim 9 including a tapered dilator shaft for use with said exchange rod for gentle expansion of said small portal to facilitate insertion of said biopsy cannula.

11. The system according to claim 10 in which said biopsy cannula comprises a larger central channel, and an auxiliary valve having an angled channel for introducing surgical instruments.

12. The system according to claim 1 in which said fiberoptic arthroscope comprises; a 30,000 pixel fiberoptic image bundle of approximately 1.2 mm diameter, illumination fibers, dual element distal lens, stainless steel sheath at a working end, a scope lock for securing said arthroscope to said handpiece and separate image and illumination plug-ins at a proximal end for connection to an optical coupler, an arthroscopic camera and a light source.

13. The system according to claim 11 including irrigation channels in said disposable handpiece; an irrigation tube connected to dual irrigation, pressurized and controlled solution storage containers; and a compressor for providing said irrigation fluid pressure through said irrigation tube to said irrigation channel for control by said irrigation valve.

14. The system according to claim 13 including a suctioning device connected to said disposable handpiece; said suctioning device comprising a suction hose connected to said disposable handpiece; a pair of collection canisters connected to a suction console; said suction console containing a vacuum pump connected to said collecting canisters for drawing fluid and loose material from within the joint through said disposable handpiece; said suction being controlled by said suction valve in said disposable handpiece.

15. The system according to claim 14 including a high resolution monitor connected to said arthroscopic camera; and a recording device for documenting the arthroscopic procedure.

16. The system according to claim 15 in which said recording device is a video recording device.

17. The system according to claim 15 in which said recording device is a video printing device.

18. The system according to claim 15 including a self-contained mobile cart for storing and transporting said video camera and light source, said high resolution monitor, said recording device, said compressor, said vacuum pump, said collecting canisters, and said irrigation solution pumps, whereby said system may be easily transported to an operation site and positioned outside of the sterile field for convenient viewing.

19. The system according to claim 18 in which an optical coupler, focussing mechanism, video camera, camera head and light source are integrated into a single enclosure off the sterile field for ease of use and minimize the components in the sterile field; whereby an interior space of said joint may be visualized, examined, diagnosed, treated, and lavaged by alternate irrigation and suction.

20. The system according to claim 1 including a coupling on an end of said disposable handpiece opposite said cannula, said coupling having a central main channel and an auxiliary angled channel, whereby an arthroscope and a biopsy instrument may be inserted through said cannula for simultaneous observation and treatment of said joint space.

21. The system according to claim 1 including a cannula attaching to the front of said disposable handpiece having a central main channel and an auxiliary angled channel, whereby an arthroscope and a biopsy instrument may be inserted through said cannula for simultaneous observation and treatment including tissue specimen biopsy.

22. The system according to claim 21 including an auxiliary valve for medication on said cannula; said angled channel passing through said cannula including a second valve for the separate insertion of a biopsy or other instrument.

23. The system according to claim 22 including an auxiliary valve on said coupling; said angled channel passing through said auxiliary valve.

24. The system according to claim 23 in which said arthroscope is inserted through said central main channel and said biopsy instrument is inserted through said auxiliary channel.

25. The system according to claim 24 in which said biopsy instrument is inserted through said central main channel and said arthroscope is inserted through said auxiliary angled channel.

* * * * *